United States Patent [19]

Lange et al.

[11] Patent Number: 5,554,166
[45] Date of Patent: Sep. 10, 1996

[54] BLOOD LANCET DEVICE FOR WITHDRAWING BLOOD FOR DIAGNOSTIC PURPOSES

[75] Inventors: Hans Lange, Lampertheim; Herbert Argauer, Pirk, both of Germany

[73] Assignee: Boehringer Mannheim GmbH, Mannheim, Germany

[21] Appl. No.: 260,811

[22] Filed: Jun. 16, 1994

[30] Foreign Application Priority Data

Jun. 21, 1993 [DE] Germany ............... 43 20 463.5

[51] Int. Cl.⁶ .................................................. A61B 17/32
[52] U.S. Cl. .................................... 606/182; 128/770
[58] Field of Search ............................. 606/181–183; 128/770

[56] References Cited

U.S. PATENT DOCUMENTS

| | | |
|---|---|---|
| 3,358,689 | 12/1967 | Higgins . |
| 4,442,836 | 4/1984 | Meinecke et al. . |
| 4,895,147 | 1/1990 | Bodicky et al. ............ 606/182 |
| 5,074,872 | 12/1991 | Brown et al. ............... 606/182 |
| 5,100,427 | 3/1992 | Crossman et al. .......... 606/182 |
| 5,196,025 | 3/1993 | Ranalletta et al. ......... 606/182 |
| 5,282,822 | 1/1994 | Macors et al. ............. 606/182 |

OTHER PUBLICATIONS

"Contamination Of A Finger–Stick Device" and Response by Shier et al. and Bohero, *New England Journal of Medicine* Apr. 1, 1993 pp. 969–970.

*Primary Examiner*—Gary Jackson
*Assistant Examiner*—William W. Lewis

[57] ABSTRACT

Blood lancet device (1) for withdrawing blood from a patient for diagnostic purposes comprises a housing (10), a lancet holder (11) movable within the housing (10) for retaining a non-rotatable lancet (4) having a plastic lancet body (31), a lancet needle (33) fixed in the lancet body (31), a lancet drive (12) to move the lancet holder in a puncturing and retraction direction, an exchangeable skin-contact part (5) having an outlet opening (6) for the lancet (4) and a contact surface (42) for pressing against a patient's skin. The skin-contact part (5) and lancet (4) form a unitary disposable item (3) which is intended for once-only use and is intended to be inserted at an anterior end (2) of the housing (10) in a single operation only as a unit with the skin-contact part (5) The skin-contact part (5) and the lancet body (31) are connected to one another through a first predetermined breaking section (52) to permit the skin-contact part (5) and the lance body (31) to be separable from one another following insertion of the disposable item (3). A second breaking section connects a protective needle cap to the lancet body and both breaking sections are severed by twisting of the protective cap.

26 Claims, 3 Drawing Sheets

BLOOD LANCET DEVICE FOR WITHDRAWING BLOOD FOR DIAGNOSTIC PURPOSES

The invention relates to a blood lancet device for withdrawing blood for diagnostic purposes, comprising a housing, a lancet holder, movable within the housing, for holding a lancet which comprises a lancet body made of a plastic material and a needle fixed in the lancet body, and a lancet drive to drive the puncturing and retraction movement of the lancet holder with a lancet held therein, the housing having, at its anterior end in the puncturing direction, an exchangeable skin-contact part with an outlet opening for the lancet, said skin-contact part being provided with a contact surface for pressing against the skin when using the blood lancet device. The skin-contact part and lancet form components of a disposable item which is intended for once-only use and can be inserted at the anterior end of the housing in a single handling operation, said disposable item being designed in such a way that the lancet can be inserted into the housing only together with the skin-contact part.

In various diseases it is necessary to test human blood for specific blood values. To this end it is often sufficient to withdraw from the body only a small quantity of blood in the form of a blood droplet by producing a small puncture wound. An especially important example is diabetes, in which the blood must be tested at regular intervals for its glucose content.

The puncture wound is commonly produced using blood lancet devices comprising a puncturing instrument and exchangeable lancets which are mutually adapted. The puncturing instrument contains the lancet holder into which one lancet at a time can be exchangeably inserted. During the puncturing operation the lancet holder with the lancet is moved rapidly in the puncturing direction until the tip of the lancet emerges from the outlet opening of the skin-contact part and produces a small puncture wound in the body part against which the skin-contact part is pressed. The lancet holder with the lancet is then retracted counter to the puncturing direction. An example of a lancet device of this type is described in U.S. Pat. No. 4,442,836.

Hereinafter, the end of the puncturing instrument bearing the outlet opening will be called the anterior end, and the opposite end will be called the posterior end.

To avoid infection, a new lancet must be used for each puncturing operation. The instrument described in the above mentioned U.S. Pat. No. is therefore designed in such a way that the used lancet is automatically ejected from the instrument following each puncturing operation, when said instrument is retensioned.

However, a risk of infection may originate not only from the lancet itself, but also from the contact surface of the puncturing instrument pressed against the skin. This applies particularly within the hospital sector and in medical practices in which the same blood-sampling instrument is used for different patients. Here, on account of the possible transfer of pathogens contained in the patients' blood, there is a high risk of infection with, for example, AIDS or hepatitis-B viruses.

In order to exclude the risk of infection via the skin-contact surface, in a known instrument of the kind described in the preamble a special skin-contact part is envisaged which is exchanged together with the lancet. With this arrangement, the lancet and the skin-contact part are two separate parts which are assembled to form a unit which can be applied at the lower end of the puncturing instrument and is intended for once-only use. Such a unit composed of a lancet and a skin-contact part which is intended for once-only use is here called a disposable item.

In the known blood lancet device, the skin-contact part is designed as a longitudinal sleeve whose length is almost a third of the overall length of the blood lancet device (when it is in the "usable state", i.e. ready for use) and completely surrounds its lower end. The lancet sits in the sleeve as a separate component, being held anteriorly by elastic plastic strips, which drive the retraction movement following the puncture. This instrument is tensioned by manually pushing back the lancet holder which, in the usable state, is covered by the sleeve-type skin-contact part. Following the puncture, the instrument can therefore be retensioned only if the skin-contact part is first removed. Although this ensures that the disposable item consisting of the skin-contact part and the lancet must be removed before the device is tensioned or reused, following removal of the disposable item and retensioning of the blood lancet device it does not reliably prevent the same disposable item from being re-inserted into the housing and re-used. Accidental or deliberate re-use of the disposable item (on account of ignorance of the associated risks) therefore cannot be excluded.

An object of the invention is therefore to reliably prevent re-use of all parts of a blood lancet device which may come into contact with the patient's blood.

In a blood lancet device of the type described in the preamble this is achieved according to the invention in that, in the disposable item, the skin-contact part and the lancet body are firmly connected to one another and at the point of connection between the skin-contact part and the lancet body a first predetermined breaking section is envisaged by means of which the skin-contact part and the lancet body are separable from one another following insertion of the disposable item.

It is characteristic of the invention that, when being inserted into the puncturing instrument, the disposable item is in an insertion state in which the skin-contact part is (directly or indirectly) firmly connected with the lancet body. This insertion state is maintained until either the skin-contact part or the lancet or both are in their end position (position for use) within the blood lancet device. In the insertion state, the blood lancet device is not usable, because the lancet body is firmly connected with the skin-contact part.

By severance at the predetermined breaking section, the disposable item is transformed from the insertion state into a usable state in which the lancet body, and therefore the lancet, is free, so that the puncturing and retraction movement for the production of a puncture wound is possible. The skin-contact part and the lancet are designed in such a way that, in the usable state following severance at the predetermined breaking section, it is practically impossible to insert them into the puncturing instrument (although it may be possible with the aid of supplementary tools such as, for example, tweezers). In particular, the skin-contact part is so small that it can in practice be attached only in conjunction with the disposable item at the anterior end of the blood lancet device. Re-use both of used lancets and of used skin-contact parts following severance at the predetermined breaking section is thereby excluded in practice.

The tip of the lancet is commonly protected with a tip-protection cap, which is connected with the lancet body via a predetermined breaking section and is removed before the lancet is used. A tip-protection cap of this type is also preferably envisaged in the case of the invention, the predetermined breaking section between the tip-protection cap and the lancet body being a second predetermined breaking section (supplementary to the first predetermined breaking section at the point of connection between the skin-contact part and the lancet body). In this embodiment, the disposable item is preferably designed in such a way that the first and second predetermined breaking sections can be severed in a single handling operation (preferably simultaneously). This simplifies handling in that the disposable item can be transformed from the insertion state into the usable state with a single movement of the hand.

The predetermined breaking section may be created using methods familiar to a person skilled in the art. Generally it is a web or strip of material which is mechanically weaker than the rest of the disposable. Thereby the component of the disposable (lancet body, skin body part and, where applicable, tip-protection cap) separate selectively at the predetermined breaking section when the disposable is put under mechanical stress such as by rotating the parts relative to each other about their longitudinal axis.

The disposable item as a whole is preferably—with the exception of the metallic lancet needle—a plastic injection moulding. With this arrangement, the lancet body, the skin-contact part and, where applicable, the tip-protection cap can be manufactured in a single operation by the plastic injection-moulding method, the needle being located in the longitudinal axis of the plastic part. With the use of this method, predetermined breaking sections may simply take the form of easily severable thin spots or webs of the injection-moulded plastic material.

The connection between the skin-contact part and the lancet body need not necessarily be direct. In an especially preferred embodiment, the skin-contact part is connected to the lancet body only indirectly, via the tip-protection cap, the first predetermined breaking section being located at the point of connection between the skin-contact part and the tip-protection cap (at the edge of the outlet opening provided in the skin-contact part), while the second predetermined breaking section is, as usual, created between the tip-protection cap and the lancet body.

A disposable item according to the invention is inexpensive to manufacture. With manufacture as a plastic injection moulding, the manufacturing costs scarcely differ from those of lancets commonly used in blood lancet devices. A low purchase price is an additional incentive to avoid the reuse of used disposable items. With the invention the tip-protection cap is used for handling the disposable item. Therefore the skin-contact part can be very small, preferably essentially as an annual plate. This compares favourably with the prior art where a big sleeve is required for handling purposes. In addition to a substantial reduction of manufacturing costs, the design of the skin-contact part as a relatively small component also results in a small overall size of the disposable item and therefore small packaging volume.

In order to make sure that the device can only be operated in a defined sequence of steps the lancet drive in a preferred embodiment has means for ensuring that repeated tensioning of the lancet drive is possible only after removal of the lancet, which during the prior puncturing and retraction movement was located in the lancet mounting. Various possibilities for performing this function are known. In U.S. Pat. No. 4,442,836 mentioned above, for example, the lancet mounting is provided with a lever arm which, during the tensioning process, abuts against a fixed projection and thereby automatically ejects the lancet. In this arrangement, therefore, tensioning of the lancet device is possible only when the used lancet is simultaneously ejected. The instrument with the sleeve-type skin-contact part, also mentioned above, has a re-tensioning lock such that the lancet holder can be pushed back only when empty. Another, especially preferred embodiment is described in greater detail below in the description of an exemplifying embodiment of the invention.

An embodiment of this type is especially advantageous because, in addition to safeguarding against re-use of a skin-contact part and/or a lancet which has been used and removed from the instrument ("re-use lock"), it ensures that the lancet which is still in the instrument cannot be used a second time. This provides virtually complete protection against risks of infection due to mis-use of the blood lancet device.

The invention is illustrated in greater detail below using an exemplifying embodiment schematically represented in the following figures.

Figure 1:
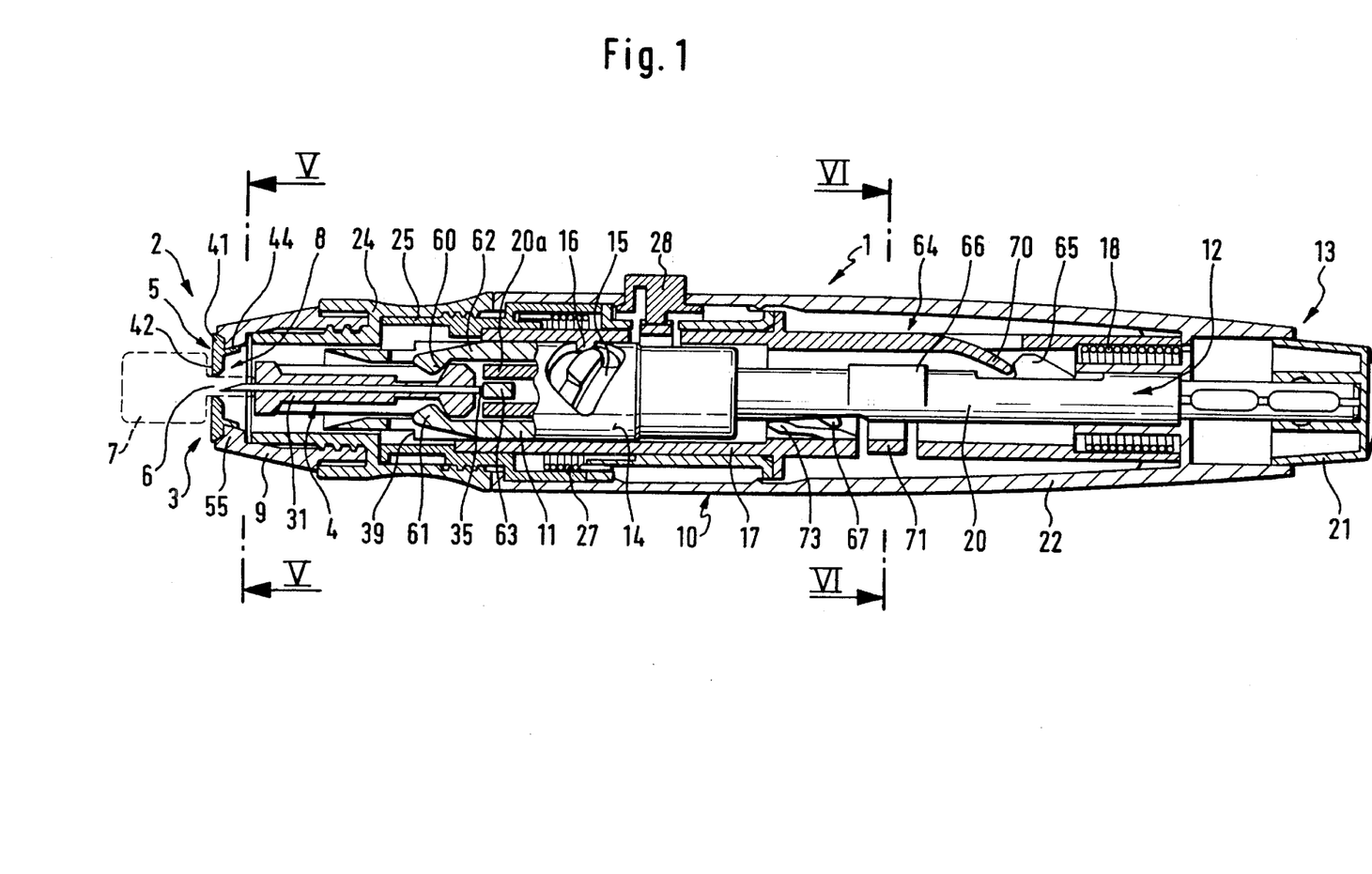
FIG. 1 A sectional view of a blood lancet device along its longitudinal axis.

FIG. 1 shows a blood lancet device 1 according to the invention with a disposable item 3 inserted at its anterior end 2. The disposable item 3 comprises a lancet 4, a skin-contact part 5 and a tip-protection cap 7. In FIG. 1 it is represented in its usable state, lancet 4 sitting in a lancet holder 11, and skin-contact part 5 being attached to an adjusting cap 9 of the housing 10 in such a way that it closes its anterior opening 8, apart from an outlet opening 6 for the lancet. The tip-protection cap 7 is removed in the usable state, and for this reason it is represented as a dashed line in FIG. 1.

In the embodiment shown, the puncturing and retraction movement of the lancet holder 11 and the lancet 4 located therein is guided by a driver cam 15, which is formed by a groove-shaped recess in the circular casing surface 14 of the lancet holder 11. With the driver cam 15 there engages a driver pin 16 of a drive sleeve 17 enclosing the lancet holder 11 in this region. The drive sleeve 17 extends within the housing 10 almost as far as the (in the puncturing direction) posterior end of the blood lancet device 1. A spirally wound coiled spring 18 within the drive sleeve 17, which drives the drive sleeve 17, is also located here. Through the coiled spring 18 runs an ejector 20 which with its anterior end 20a engages with the lancet holder 11 and which has an operating button 21 disposed at its posterior end. The drive sleeve 17 is in operative connection with an intermediate ring 25, which is permanently secured with a tensioning ring 24, on to which the adjusting cap 9 can be screwed.

For tensioning of the blood lancet device 1, the housing 10 is held by its upper sleeve part 22, and the tensioning ring 24 with the intermediate ring 25 and hence the drive sleeve 17 is rotated to the right (when viewed counter to the puncturing direction). This movement is conveyed via the drive sleeve 17 to the coiled spring 18. At the end of the tensioning movement an arresting device, not shown, stops the drive sleeve, causing the coiled spring 18 to remain in the tensioned state. A return spring 27 rotates the intermediate ring 25 with the tensioning ring 24 through a left-hand movement relative to the drive sleeve 17 into its initial state.

The lancet drive, which in its entirety is given the number 12, is essentially formed by the coiled spring 18, the drive sleeve 17, the driver pin 16, the driver cam 15 and the ejector 20, which simultaneously provides a torsion protection means. If the lancet drive is released by a disengaging element 28, the drive sleeve 17 and the driver pin 16 disposed thereon make a left-hand rotation (when viewed counter to the puncturing direction). With this arrangement, driver pin 16 travels along the driver cam 15, as a result of which the lancet holder 11 and the lancet 4 located therein execute the puncturing and retraction movement.

More precise details concerning the lancet drive used in this exemplifying embodiment may be found in German published patent application 42 12 315.

Figure 2:
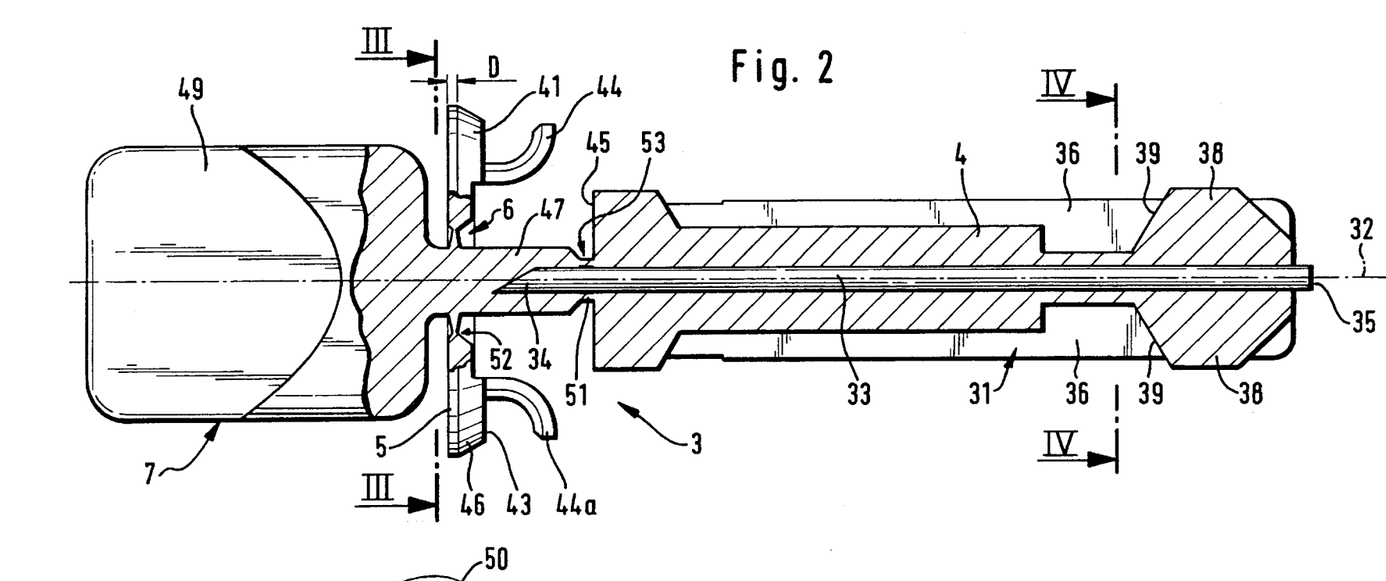
FIG. 2 A partially cutaway side view of a disposable item.
Figure 4:
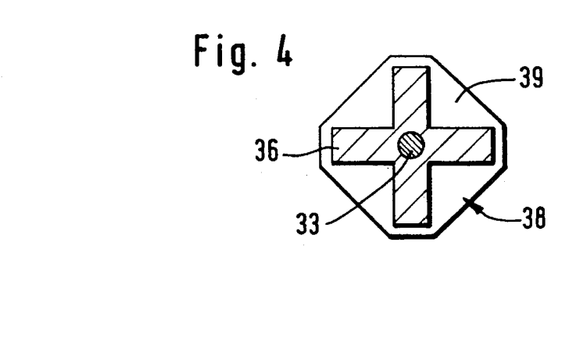
FIG. 4 A sectional view along line IV—IV in FIG. 2.

In FIG. 2, the disposable item 3 is represented in its insertion state prior to the separation of its components, the lancet 4, skin-contact part 5 and tip-protection cap 7. The lancet 4 has a lancet body 31 made of a plastic material, in which a metallic lancet needle 33 extends along its longitudinal axis 32, which is represented as a dashed line. Both ends of the lancet needle 33 project out of the lancet body 31. The anterior end of the lancet needle 33 in the puncturing direction is formed as a sharp point 34, while the posterior end has a stop surface 35. By contrast with otherwise commonly used lancets the stop surface, which is used for positioning of the lancet 4 within the lancet holder 11, is provided at the lancet needle 33, and not the lancet body. In this way, exactly reproducible puncturing depths can be achieved in the course of successive punctures with different lancets, especially when small puncture depths are used. More precise details concerning this aspect can similarly be found in German patent application 42 12 315. In the lancet described here, the lancet body has four uniform webs 36 extending along its entire length, disposed at 90° intervals about the longitudinal axis 32, so that in cross-section they form a cross (FIG. 4). An intermediate body 38 with inclined contact-pressure surfaces 39 is located between the webs in the vicinity of the posterior end of the lancet body 31.

The skin-contact part 5 essentially comprises a disc-like ring-shaped part 41 and, moulded on to it, two hook-like engaging elements 44, which are used for attachment to the adjusting cap 9. The anterior surface of the skin-contact part 5 forms the contact surface 42, with which the blood lancet device 1 is pressed against the skin. The distance between the engaging elements 44, which are bent like hooks away from the longitudinal axis 32, is greater than the diameter of the front face 45 of the lancet body 31. The outlet opening 6 for the lancet tip 34 is located in the centre of the ring-shaped part 41 (represented in FIG. 1 in the usable state).

As previously mentioned, the skin-contact part must for various reasons be as small as possible. The diameter is at most as large as the diameter of the anterior end 2 of the blood lancet device 1. The dimension in the direction of the longitudinal axis 32, including the attachment elements, is less than 1 cm, preferably less than 5 mm. The corresponding dimension of the part of the skin-contact part which in the insertion state is accessible from the outside should be considerably smaller, to make separate insertion of the skin-contact part 5 impossible in practice. In the exemplifying embodiment represented, the skin-contact part 5 projects beyond the anterior end 2 of the blood lancet device 1 only by the length D shown in FIG. 2. This dimension should generally be less than 2 mm. In the preferred embodiment, it is less than 1 mm.

Figure 5:
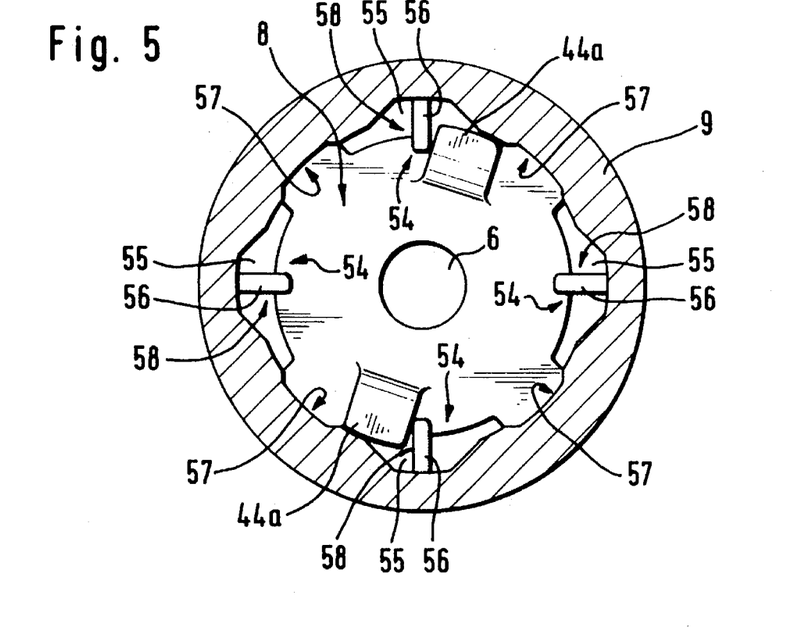
FIG. 5 A sectional view along line V—V in FIG. 1.

As can be seen in FIG. 5, the adjusting cap 9 has means of attachment 54 for the exchangeable attachment of the skin-contact part 5. In the embodiment represented, the attachment functions as a type of bayonet fastening. Along a circumferential line of the opening 8 of the adjusting cap 9 there extend four shoulders 55. Behind each shoulder 55, a web 56 serving as a rotation-limiting stop 58 is centrally disposed. A guide recess 57 is located between each pair of shoulders 55.

FIG. 2 shows that the tip-protection cap 7 extends through the outlet opening 6 with a shaft 47 and, in the section in front of the outlet opening 6, has a gripping zone 49 for handling the disposable item 3. The diameter of the opening 6 should be smaller than 3.5 mm and preferably measure about 2 to 2.8 mm.

Figure 3:
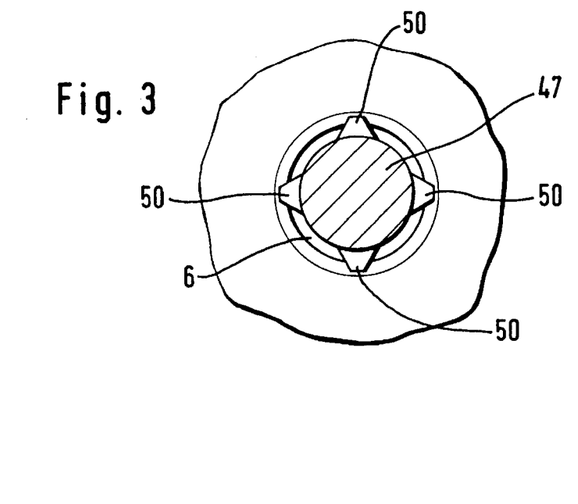
FIG. 3 A sectional view along line III—III in FIG. 2.

The tip-protection cap 7 is connected with the skin-contact part 5 by means of four webs 50 evenly distributed around the boundary surface of the outlet opening 6 (FIG. 3). The webs 50 are designed in such a way that they break when the tip-protection cap 7 is rotated, and thus form the first predetermined breaking section 52. The connection between the tip-protection cap 7 and the lancet body 31 is formed by a thin-walled surrounding web 51 between the front face 45 of the lancet body 31 and the shaft 47 of the tip-protection cap 7. This web 51 forms the second predetermined breaking section 53.

To accommodate the lancet 4, the lancet holder 11 represented in FIG. 1 has an accommodating recess which in cross-section is essentially square. The square recess is adapted to the webs 36 (FIG. 4) of the lancet body 31 in such a way that the lancet body 31 can be introduced into the lancet holder 11 in four different positions, each turned through 90° about the longitudinal axis 32. The skin-contact part 5 with the engaging elements 44 can also be introduced into the guide recesses 57 (FIG. 5) of the adjusting cap 9 in these four positions. Two lugs 61 provided with sloping edges 60 project into the accommodating recess of the lancet holder 11, said lugs each being located on elastically deflectable tensioning tongues 62. In addition, when viewed counter to the puncturing direction a stop element 63 is provided at the rear end of the accomodating recess running transversely to the puncturing direction.

To insert the disposable item 3 the lancet 4 is introduced against the pressure of the tensioning tongues 62 into the lancet holder 11 with the lancet drive 12 tensioned. Thereby the ejector 20 is pushed backwards. At the same time, the lugs 61 slide on the intermediate bodies 38 of the lancet body 31, said intermediate bodies being adjacent each lug. Towards the end of the insertion movement, the two lugs 61 reach the contact-pressure surface 39 with their sloping edge 60, as a result of which the disposable item 3 is drawn into the lancet holder 11. The insertion movement is completed when the contact-pressure surface 35 touches the stop web 63. Simultaneously, the two engaging elements 44 are introduced into the adjusting cap 9 via two of the recesses 57, so that the hook-like ends 44a of the two engaging elements 44 are located at roughly the same longitudinal position as the stop webs 56.

In this position the disposable item 3 is inserted into the blood lancet device 1. In general, insertion of the disposable item is considered "complete" for the purpose of the invention when at least one of the two main components of the disposable item, namely the lancet 4 and the skin-contact part 5, has reached its end position in the direction of the puncturing movement. In the embodiment represented this is the lancet 4, which is located in the lancet holder 11 in its operating position.

Since in the insertion state the predetermined breaking sections are still intact, the blood lancet device 1 is not yet usable. In order to convert it into the usable state, the second predetermined breaking section between the lancet body 31 and the tip-protection cap 7 must first be severed by left-hand or right-hand rotation of the tip-protection cap 7. By further rotation of the tip-protection cap 7 in the same direction as before, the engaging elements 44 impinge against the corresponding stop webs 56. In this position the ends 44a of the engaging elements 44 each engage with a shoulder 55. Due to this engagement and by abutment of the conical circumferential surface 46 of the ring-shaped part 41 against a congruent surface of the adjusting cap 9, a reliable axial and radial positioning of the skin-contact part 5 is ensured. Continuation of the rotary movement of the tip-protection cap 7 causes the four webs 50 to break, thereby severing the first predetermined breaking section 52.

The two predetermined breaking sections have thus been severed in a single handling operation, namely rotation of the tip-protection cap 7, as a result of which the blood lancet device 1 has been transformed from the insertion state into the usable state. In the separated state, the individual elements of the disposable item 3 cannot be re-inserted (or only with the aid of a tool and with considerable effort, which precludes accidental mis-use).

In the preferred embodiment described, means 64 (FIG. 1) are provided by which it is ensured that repeated tensioning of the lancet drive is possible only after removal of the lancet which during the prior puncturing and retraction movement is located in the lancet mounting. These means are described below.

Figure 6:
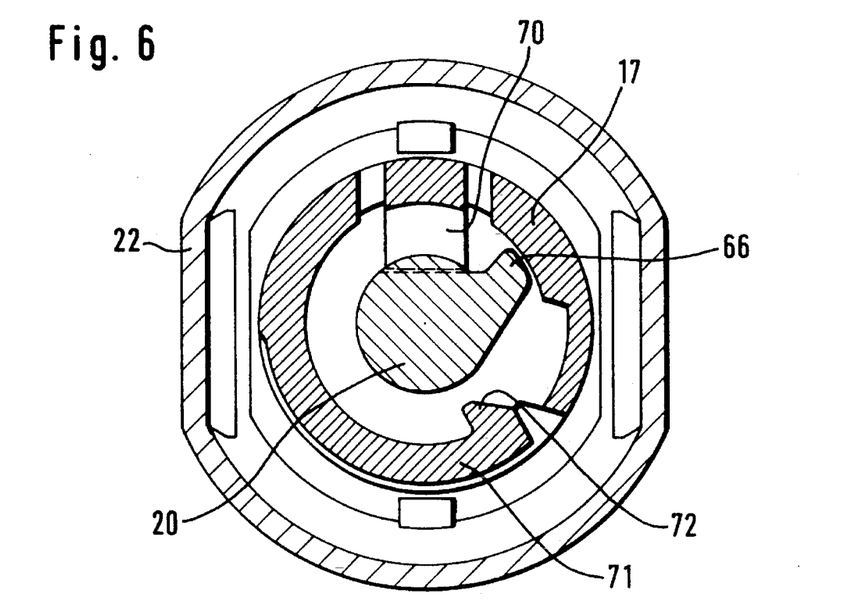
FIG. 6 A sectional view along line VI—VI in FIG. 1.

On its casing surface, the ejector 20 is provided with an ejection-protection lug 65 which in the puncturing direction slopes upwards in a ramp-like fashion. Further forwards and offset relative to the ejection-protection lug 65 on the circumference, the ejector 20 also has a pin 66 (FIG. 1 and FIG. 6). In front of the pin 66 and offset relative to it and to the ejection-protection lug 65 on the circumference of the ejector 20, there is a pushback protection lug 67 on the casing surface of the ejector 20 which slopes upwards in a ramp-like fashion counter to the puncturing direction. The anterior end 20a of the ejector 20 is designed in the form of a fork in such a way as to be axially movable within the lancet holder 11 in the region of the stop element 63.

FIG. 1 shows that the drive sleeve 17 in the vicinity of its posterior end has a first elastic locking tongue 70 which follows an initially axially parallel course and is then bent slightly inwards, and which projects into the drive sleeve 17. Further forwards in the puncturing direction, the drive sleeve 17 has a second elastic locking tongue 71 which follows an arc-shaped course roughly along a circum-ferential line. The free end of the second elastic locking tongue 71 is provided with a lug 72 which projects into the interior of the drive sleeve 17, said lug being offset relative to the first locking tongue 70 (FIG. 6) on the circumference. In front of the second locking tongue 71, another axially directed third elastic locking tongue 73 is present on the drive sleeve 17. This is positioned on the internal surface of the drive sleeve and forms a deflectable ramp which slopes upwards in the puncturing direction.

The drive sleeve 17 is now co-ordinated with the ejector 20 in such a way that, during a puncturing and retraction movement of the lancet 4, the pin 66 of the ejector 20 and the second locking tongue 71, as shown in FIG. 1 and FIG. 6, are located at the same height. This movement of the lancet 4 is effected by a left-hand rotation of the drive sleeve 17 (as represented in FIG. 6). With this arrangement, the lug 72 of the second locking tongue 71 moves over the pin 66 and engages behind it.

Because the ejector 20 is protected against rotary movements, the right-hand rotation of the drive sleeve 17, which is necessary for tensioning, is not possible. The disposable item 3 must therefore first be ejected in its individual parts by operating the ejector 20. The fork-like anterior end 20a of the ejector 20 here pushes the lancet 4 out of the lancet holder 11 via axial longitudinal displacement of lancet 4.

The lancet body 31 in turn pushes with its front face 45 on the ring-shaped part 41 between the engaging elements 44. As a result, the hook-like ends of the engaging elements 44 move over the shoulders 55. The skin-contact part 5 and lancet 4 are then ejected.

Due to this axial displacement of the ejector 20, the pin 66 now releases the second locking tongue 71. Right-hand rotation of the drive sleeve 17, and hence tensioning of the blood lancet device 1, is now possible. However, during the ejection movement of the ejector 20 the pushback protection lug 67 has also moved over the third locking tongue 73 and engaged behind it. Pushing back the ejector 20, which is necessary for insertion of a disposable item 3, is therefore impossible. The blood lancet device 1 must of necessity first be tensioned by right-hand rotation of the drive sleeve 17. The pushback protection lug 67 is thereby also rotated relative to the locking tongue 73, and thus released.

The next step is the introduction of the disposable item 3, as a result of which the ejector 20 is pushed back by pressing the lancet body 31 against the anterior end of the ejector 20. During this procedure, the ejection-protection lug 65 moves away under the first locking tongue 70 due to deflection of the latter. The ejection-protection lug 65 at the same time engages with the locking tongue 70 as soon as the disposable item has reached its insertion state in the blood lancet device 1. Engagement of the locking tongue 70 with the ejection-protection lug 65 prevents (for example unintentional) ejection of the disposable item 3 before it has been transformed into the usable state and the lancet has executed the puncturing and retraction movement.

Overall, this results in fully constrained guidance of the operating steps for tensioning, insertion of the disposable item, severance of the predetermined breaking sections, triggering of the puncturing process, and ejection of the lancet.

We claim:

1. Blood lancet device for withdrawing blood for diagnostic purposes, comprising:
    a housing,
    a lancet holder, movable within the housing, for holding a lancet, said lancet being a component of a disposable item which comprises the lancet with a lancet body made of a plastic material, an exchangeable skin contact part and a lancet needle fixed in the lancet body, and which disposable item is intended for once only use and is inserted at an anterior end of the housing in a single operation,
    a lancet drive to drive the puncturing and retraction movement of the lancet holder with a lancet held therein,
    wherein the housing has an anterior end in the puncturing direction, receiving the exchangeable skin-contact part and the lancet,
    said exchangeable skin-contact part having a contact surface for pressing against the skin when using the blood lancet device and an outlet opening for the lancet,
    wherein said disposable item is configured such that the lancet can be inserted only together with the skin-contact part, and
    wherein the skin-contact part and lancet body are connected to one another and at the point of connection between the skin-contact part and the lancet body, a first predetermined breaking section is provided by means of which the skin-contact part and the lance body are separable from one another following insertion of the disposable item.

2. Blood lancet according to claim 1, wherein the lancet has a tip-protection cap made of a plastic material which is connected with the lancet body via a second predetermined breaking section, and wherein both predetermined breaking sections are separated following insertion of the disposable item.

3. Blood lancet device according to claim 2, wherein the disposable item is configured such that the first predetermined breaking section and the second predetermined breaking section are separable in a single operation.

4. Blood lancet device according to claim 3 wherein, after insertion of the disposable item, the lancet holder holds the lancet non-rotatably and a rotation-limiting stop for the skin-contact part is provided at the anterior end of the housing, and wherein both predetermined breaking sections are separable by rotation of the tip-protection cap relative to the lancet and the skin-contact part.

5. Blood lancet device according to claim 2, wherein the tip-protection cap is connected with the skin-contact part at an edge of the outlet opening, and wherein the first predetermined breaking section is provided at this connection.

6. Blood lancet device according to claim 5, wherein the skin-contact part is disposed in front of the lancet body in the puncturing direction, and the tip-protection cap extends through the outlet opening of the skin-contact part.

7. The blood lancet device according to claim 2, wherein separation of the breaking sections allows for removal of the tip-protection cap while at the same time allows for retention of the skin-contact part in the housing.

8. The blood lancet device according to claim 7, wherein the separation of the breaking sections causes removal of a central portion of the skin-contact part to provide a clear passageway through the outlet opening for passage of a sharp end portion of the needle during the puncturing operation.

9. Blood lancet device according to claim 1, wherein the skin-contact part is configured ring-shaped.

10. Blood lancet device according to claim 1, wherein the lancet drive has a tension spring and means for ensuring that repeated tensioning of the lancet drive is permitted only after removal of a lancet, which during the preceding puncturing and retraction movement was located in the lancet holder.

11. The blood lancet device of claim 1, wherein the lancet body is of such shape that it cannot be removed from the housing without removal of the skin contact part from the housing.

12. A disposable blood lancet device for insertion into a lancet driver for use in withdrawing blood for diagnostic purposes, said disposable lancet device comprising a lancet body made of a plastic material, an exchangeable skin contact part and a lancet needle fixed in the lancet body, the exchangeable skin-contact part being attached to the lancet body, said exchangeable skin-contact part having a contact surface for pressing against the skin when using the disposable blood lancet device, wherein the disposable lancet device is intended for once-only use and can be inserted into an anterior end of a lancet driver in a single handling operation, wherein the skin-contact part and lancet body are connected to one another by a first predetermined breaking section by means of which the skin-contact part and the lancet body are separable from one another following insertion of the disposable item.

13. The disposable blood lancet device according to claim 12, having a tip-protection cap made of a plastic material which is connected with the lancet body via a second predetermined breaking section, and wherein both predetermined breaking sections are configured for separation following insertion of the disposable lancet device into the lancet driver.

14. The disposable blood lancet device according to claim 13, which is configured such that the first predetermined breaking section and the second predetermined breaking section are separable in a single operation.

15. The disposable blood lancet device according to claim 14 wherein both predetermined breaking sections are separable by rotation of the tip-protection cap relative to the lancet body.

16. The disposable blood lancet device according to claim 12, having a tip-protection cap that is connected with the skin-contact part, and wherein the first predetermined breaking section is provided at this connection.

17. The disposable lancet device according to claim 6 wherein the first predetermined breaking section is provided between the tip-protection cap and the skin contact part.

18. The disposable blood lancet device according to claim 12, wherein the skin-contact part is configured ring-shaped surrounding an outlet opening for said needle.

19. The disposable blood lancet device according to claim 18, wherein the skin-contact part is disposed in front of the lancet body in the puncturing direction, and the tip-protection cap extends in front of the skin-contact part and through the outlet opening of the skin-contact part.

20. The disposal blood lancet device of claim 12 wherein the lancet needle has a sharp point and is fixed in the lancet body with its sharp point positioned posterior to the skin-contact part and wherein separation of the skin-contact part from the lancet body provides an opening through the skin-contact part for movement of the needle point therethrough during a skin puncturing operation.

21. A method for puncturing the skin of a patient for withdrawing blood for diagnostic purposes utilizing a lancet driver for driving a tip of a needle of a disposable lancet device into the patients skin comprising;

inserting a disposable lancet device comprising a lancet body a lancet needle fixed in the lancet body, and an exchangeable skin-contact part as a unit into an anterior end of a housing of the lancet driver with the lancet body and needle being located within said housing of the said lancet drive and with a surface of the skin-contact part extending outwardly of the lancet driver housing, breaking a breaking section connecting the lancet body and the skin-contact part to disconnect the skin-contact part form the lancet body without removing the skin-contact part from being held by the housing, placing the outward surface of the skin-contact part against the skin of the patient without removing the skin contact part from being held by the housing;

actuating the lancet driver to cause the lancet body to move toward the anterior end of the lancet driver housing and relative to the skin-contact part wherein a tip of the needle fixed in the lancet body passes through the skin-contact part and into the patients skin.

22. The puncturing method of claim 21 wherein the disposable lancet device inserted into the housing of the lancet driver is provided with a needle tip protecting cap that covers the tip of the needle and is unitary with the disposable lancet device, and wherein the needle tip protecting cap is removed and separated from the disposable lancet device prior to the placement of the outward surface of the skin-contact part against the skin of the patient.

23. The puncturing method of claim 22 wherein the breaking of the breaking section connecting the skin-contact part from the lancet body occurs simultaneously with the separation of the needle tip protector cap.

24. The puncturing method of claim 23 wherein the needle tip protector is separated from the skin-contact part by rotation of the needle tip protector relative to the skin-contact part.

25. The puncturing method of claim 24 wherein the holding of the disposable lancet by the driver housing after insertion prevents rotation of the skin-contact part and the lancet body without preventing rotation of the needle tip protector.

26. The puncturing method of claim 21 wherein the lancet body is expelled from the housing after puncturing and wherein during this expulsion the lancet body abuts the skin-contact part and also causes the skin-contact part to be expelled from the housing.

* * * * *

UNITED STATES PATENT AND TRADEMARK OFFICE
CERTIFICATE OF CORRECTION

PATENT NO. : 5,554,166
DATED : September 10, 1996
INVENTOR(S) : Lange, et. al.

It is certified that error appears in the above-indentified patent and that said Letters Patent is hereby corrected as shown below:

Title page, before the Abstract, insert--Attorney, Agent, or Firm: Barnes & Thornburg--.

Signed and Sealed this

Twenty-sixth Day of August, 1997

Attest:

BRUCE LEHMAN

Attesting Officer

Commissioner of Patents and Trademarks